United States Patent
Khan et al.

(10) Patent No.: US 9,012,704 B2
(45) Date of Patent: Apr. 21, 2015

(54) METHODS FOR THE SYNTHESIS OF 13C LABELED IODOTRIDECANE AND USE AS A REFERENCE STANDARD

(71) Applicant: Phenomenome Discoveries Inc., Saskatoon, Saskatchewan (CA)

(72) Inventors: M. Amin Khan, Morgan Hill, CA (US); Paul L. Wood, Harrogate, TN (US); Dayan Goodenowe, Saskatoon (CA)

(73) Assignee: Phenomenome Discoveries Inc., Saskatoon, Saskatchewan (CA)

( * ) Notice: Subject to any disclaimer, the term of this patent is extended or adjusted under 35 U.S.C. 154(b) by 0 days.

(21) Appl. No.: 14/359,096

(22) PCT Filed: Nov. 16, 2012

(86) PCT No.: PCT/CA2012/001055
§ 371 (c)(1),
(2) Date: May 17, 2014

(87) PCT Pub. No.: WO2013/071413
PCT Pub. Date: May 23, 2013

(65) Prior Publication Data
US 2014/0309464 A1    Oct. 16, 2014

Related U.S. Application Data

(60) Provisional application No. 61/561,219, filed on Nov. 17, 2011.

(51) Int. Cl.
| | | |
|---|---|---|
| *C07C 17/16* | (2006.01) | |
| *C07C 19/07* | (2006.01) | |
| *C07B 59/00* | (2006.01) | |

(52) U.S. Cl.
CPC ............... *C07C 17/16* (2013.01); *C07C 19/07* (2013.01); *C07B 59/00* (2013.01)

(58) Field of Classification Search
CPC ............................ C07C 17/16; C07C 19/07
USPC ................................................. 570/181, 252
See application file for complete search history.

(56) References Cited

U.S. PATENT DOCUMENTS

2007/0055084 A1   3/2007   Stegmann et al.

OTHER PUBLICATIONS

Office Action for Canadian Patent Application No. 2,812,885 (mailed Jul. 5, 2014).
CAS Registry Nos. (1984) 86128-03-2, butane-1-13C, 1-chloro-(9C1); 58454-31-2, pentane-1-13C, 1-bromo-(9C1); 84628-46-6, pentane-2-13C, 1-bromo-(9C1); 85615-45-2, butane-1-13C, 1-bromo-(9C1); 84628-59-1, butane-2-13C, 1-bromo-(9C1); 19905-77-2, heptadecane-1-13C, 1-bromo-(8C1).
CAS Registry Nos. (1984) 59669-18-0, 1-tridecano1-1-13C (9C1); 35599-77-0, tridecyl iodide.
Yuan et al., "Synthesis of [1, 2, 3, 4, 5-13C5] Palmitic Acid (1)," Journal of Labelled Compounds and Radiopharmaceuticals 21(6):525-532 (1984).
Gilpin et al., "Synthesis of 13C Labeled n-Alkylchlorosilanes," Journal of Labelled Compounds and Radiopharmaceuticals 21(4)299-305 (1984).
Sparrow et al., "Synthises of Carbon-13-Labeled Tetradecanoic Acids," Journal of Lipid Research 24 (7):938-941 (1983).
Heusler et al., "Synthesis of N-Alkane Derivatives Labelled With Several 13C," Journal of Labelled Compounds 11(1):37-42 (1975).
Fiaux et al., "The Mass Spectrometric Fragmentation of 1-Alkyl Ions Derived From Halides," Helvetica Chimica Acta 57(3):708-721 (1974).
International search report and written opinion for corresponding application No. PCT/CA2012/001055, mailed Feb. 18, 2013.

*Primary Examiner* — Shailendra Kumar
(74) *Attorney, Agent, or Firm* — LeClairRyan, a Professional Corporation

(57) ABSTRACT

A method for preparing $^{13}$C labeled iodotridecane represented by Formula A:

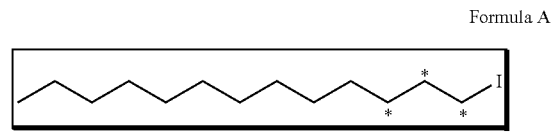

Formula A

The method comprises the conversion of $^{13}$C labeled propargyl alcohol to $^{13}$C labeled iodotridecane via alkylation of propargyl alcohol with iododecane.

20 Claims, No Drawings

METHODS FOR THE SYNTHESIS OF 13C LABELED IODOTRIDECANE AND USE AS A REFERENCE STANDARD

This application is a national stage application under 35 U.S.C. §371 of PCT Application No. PCT/CA2012/001055, filed 16 Nov. 2012, which claims the priority benefit of U.S. Provisional Patent Application Ser. No. 61/561,219, filed 17 Nov. 2011.

FIELD OF INVENTION

The present invention relates to a process for the synthesis of haloalkanes, haloalkenes and haloalkynes, and specifically, for the synthesis of $^{13}C$ labeled haloalkanes haloalkenes and haloalkynes. In an embodiment, the synthesis of $^{13}C$. labeled iodotridecane is provided.

BACKGROUND OF THE INVENTION

The haloalkanes, haloalkenes and haloalkynes are a group of hydrocarbon compounds containing one or more halogens, such as iodine, bromine, chlorine or fluorine. They have a wide variety of uses and applications. Of particular interest to the present invention are haloalkanes, haloalkenes and haloalkynes labeled with one or more $^{13}C$ atoms, and methods for their synthesis.

The particular haloalkanes, haloalkenes and haloalkynes described herein are useful building blocks for chemical syntheses of a variety of molecules, for instance, in the preparation of $^{13}C$ labeled plasmalogen molecules.

SUMMARY OF THE INVENTION

An object of the invention is accordingly to provide useful methods to produce $^{13}C$ labeled haloalkanes, haloalkenes and haloalkynes, including but not limited $^{13}C$ labeled iodotridecan.

In an aspect of the invention, a process is provided for preparing a $^{13}C$ labeled haloalkane, haloalkene or haloalkyne as represented by Formula (i):

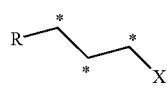

Formula (i)

wherein R is a $C_1$-$C_{28}$ carbon chain comprising up to 6 double or triple bonds, more preferably a $C_5$-$C_{20}$ carbon chain comprising up to 5 double bonds, even more preferably a $C_{10}$ carbon chain comprising no double or triple bonds, X is a halogen, preferably F, Cl, Br or I, more preferably I, and the compound of Formula (i) is $^{13}C$ labeled at one or more of the carbon atoms labeled with an asterisk, more preferably at two or more, and even more preferably at all three of the carbon atoms labeled with an asterisk. The process comprises:

(a) protecting the primary alcohol present in $^{13}C$ labeled propargyl alcohol by ether bond formation to obtain a compound of Formula (ii):

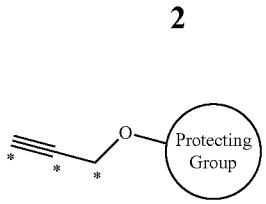

Formula (ii)

wherein the $^{13}C$ labeled propargyl alcohol is labeled at $C_1$, $C_2$ or $C_3$ thereof, or a combination thereof, and the compound of Formula (ii) is $^{13}C$ labeled at one or more of the carbon atoms labeled with an asterisk; preferably by reaction with dihydropyran (DHP) and p-toluenesulfonic acid (PTSA) to produce a compound represented by Formula 2:

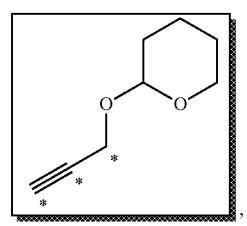

Formula 2

(b) alkylating the compound of Formula (ii) with X—R, wherein R is as defined above, and X is a halogen, preferably F, Cl, Br or I, more preferably I, to obtain a compound as represented by

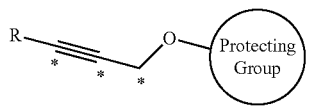

Formula (iii)

wherein the compound of Formula (iii) is $^{13}C$ labeled at one or more of the carbon atoms labeled with an asterisk; preferably the protecting group is a tetrahydropyran (THP) group, and the compound of Formula (ii) is alkylated with a halodecane, more preferably iododecane, to obtain a compound as represented by Formula 3:

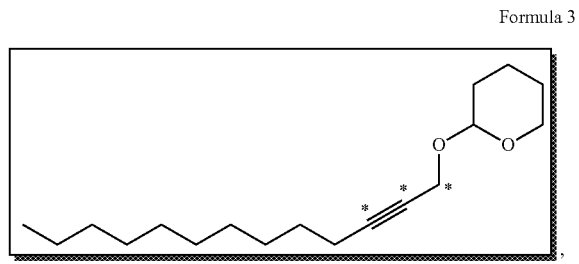

Formula 3

(c) hydrogenating the compound of Formula (iii) to obtain a compound as represented by Formula (iv):

Formula (iv)

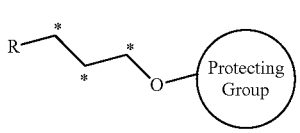

wherein the compound of Formula (iv) is $^{13}$C labeled at one or more of the carbon atoms labeled with an asterisk; and preferably at all three carbon atoms;

(d) removing the protecting group in the compound of Formula (iv) to obtain the compound of Formula (v):

Formula (v)

wherein the compound of Formula (v) is $^{13}$C labeled at one or more of the carbon atoms labeled with an asterisk; and preferably at all three carbon atoms; and (e) halogenating the primary alcohol present in the compound represented by Formula (v) to obtain the compound of Formula (i), preferably, by fluorination, chlorination, bromination or iodination, more preferably by iodination.

In one non-limiting embodiment of the invention, a process is provided for preparing $^{13}$C labeled iodotridecane as represented by Formula A Formula A

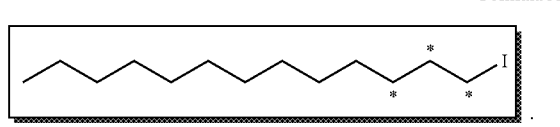

In this process, the primary alcohol present in $^{13}$C labeled propargyl alcohol is protected by ether bond formation, i.e. by reaction with dihydropyran (DHP) and p-toluenesulfonic acid (PTSA) to produce a compound represented by Formula 2:

Formula 2

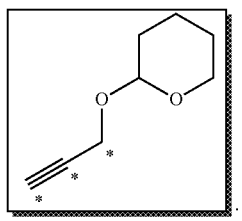

In certain non-limiting embodiments, the compound of Formula 2 can be obtained with a yield of 82%-92%.

The compound of Formula 2 thus obtained is then alkylated with iododecane to obtain a compound as represented by Formula 3:

Formula 3

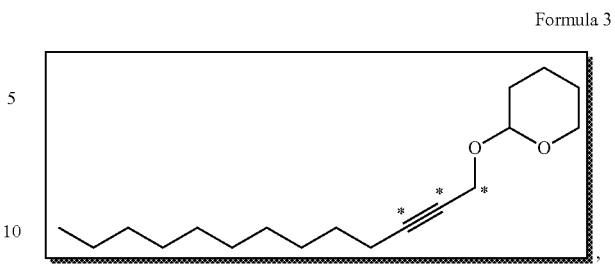

In certain non-limiting embodiments, the compound of Formula 3 can be obtained with a yield of 42%-92%.

The compound represented by Formula 3 is then hydrogenated to obtain a compound as represented by Formula 4:

Formula 4

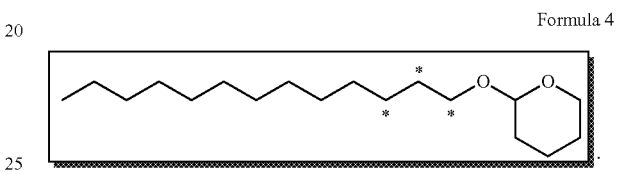

In certain non-limiting embodiments, the compound of Formula 4 can be obtained with a yield of 85%-95%.

Tetrahydropyran (THP) present in the compound of Formula 4 is then removed in a deprotection reaction to obtain a compound represented by Formula 5:

Formula 5

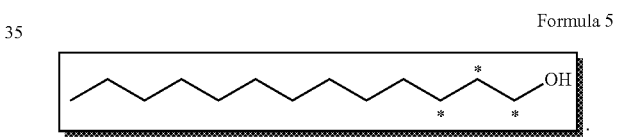

In certain non-limiting embodiments, the compound of Formula 5 can be obtained with a yield of 85%-95%.

Finally, iodination of the primary alcohol present in the compound represented by Formula 5 is carried out to obtain the compound represented by Formula A. In certain non-limiting embodiments, the compound of Formula A can be obtained with a yield of 80-88%.

In a preferred embodiment, which is non-limiting, the step of protecting the primary alcohol of the $^{13}$C propargyl alcohol to yield the compound represented by Formula 2 is carried out in the presence of dichloromethane, p-toluenesulfonic acid (PTSA) and dihydropyran (DHP) at about room temperature.

In yet another embodiment, which is also considered non-limiting, the alkylation reaction carried out to obtain the compound represented by Formula 3 is carried out in the presence of tetrahydrofuran (THF), hexamethylphosphoramide (HPMA) and n-BuLi at a temperature of between about −78° C. to about room temperature.

In a further non-limiting embodiment, the hydrogenation reaction used to obtain the compound represented by Formula 4 is carried out in a hydrogen atmosphere in the presence of ethyl acetate and palladium on carbon (Pd/C).

In another non-limiting embodiment, the deprotection step used to obtain the compound represented by Formula 5 is carried out in the presence of methanol and PTSA at about room temperature.

In yet another embodiment, also considered to be non-limiting, the iodinization step to produce the compound represented by Formula A is carried out in the presence of dichloromethane, triphenyl phosphine and imidazole at a temperature of between about 0° C. to about room temperature.

DETAILED DESCRIPTION

Described herein is a process for chemically preparing $^{13}C$ labeled haloalkanes, haloalkenes and haloalkynes as represented by Formula (i):

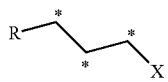

Formula (i)

wherein R is a $C_1$-$C_{28}$ carbon chain comprising up to 6 double or triple bonds. In certain no-limiting embodiments R is a $C_5$-$C_{20}$ carbon chain comprising up to 5 double bonds, or a $C_{10}$ carbon chain comprising no double or triple bonds. X is a halogen, such as F, Cl, Br or I, and the compound of Formula (i) is $^{13}C$ labeled at one or more of the carbon atoms labeled with an asterisk. In certain embodiments it may be desired to have two or more, or even all three of the carbon atoms with an asterisk $^{13}C$ labeled. The process comprises:

(a) protecting the primary alcohol present in $^{13}C$ labeled propargyl alcohol by ether bond formation to obtain a compound of Formula (ii):

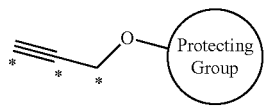

Formula (ii)

wherein the $^{13}C$ labeled propargyl alcohol is labeled at $C_1$, $C_2$ or $C_3$ thereof, or a combination thereof, and the compound of Formula (ii) is $^{13}C$ labeled at one or more of the carbon atoms labeled with an asterisk, (b) alkylating the compound of Formula (ii) with X—R, wherein R is as defined above, and X is a halogen, to obtain a compound as represented by Formula (iii):

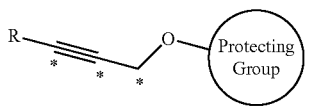

Formula (iii)

wherein the compound of Formula (iii) is $^{13}C$ labeled at one or more of the carbon atoms labeled with an asterisk; and in certain non-limiting embodiments the protecting group is a tetrahydropyran (THP) group, (c) hydrogenating the compound of Formula (iii) to obtain a compound as represented by Formula (iv):

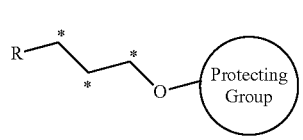

Formula (iv)

wherein the compound of Formula (iv) is $^{13}C$ labeled at one or more of the carbon atoms labeled with an asterisk, (d) removing the protecting group in the compound of Formula (iv) to obtain the compound of Formula (v):

Formula (v)

wherein the compound of Formula (v) is $^{13}C$ labeled at one or more of the carbon atoms labeled with an asterisk, (e) halogenating the primary alcohol present in the compound represented by Formula (v) to obtain the compound of Formula (i), for instance but not limited to using fluorination, chlorination, bromination or iodination reactions.

In one non-limiting embodiment, a process for preparing $^{13}C$ labeled iodotridecane is described. In certain embodiments of the described process a highly pure product can be obtained, and at reduced cost as compared to other methods through the use of generally abundant and inexpensive reagents. The process also has the advantage that, in certain embodiments, no downstream processing is required. In addition, because a highly pure iodotridecane product can be obtained in certain non-limiting embodiments of the described process, the relative amount of iodotridecane that is needed in the end application(s) is reduced, which can further reduce costs.

It will be appreciated by those skilled in the art that each of the embodiments of the invention described herein may be utilized individually or combined in one or more manners different than the to ones disclosed above to produce an improved process for the production of $^{13}C$ labeled haloalkanes, haloalkenes and haloalkynes. In addition, those skilled in the art will be able to select a suitable temperature in view of the reaction conditions being used, in further embodiments of the invention encompassed herein.

Unless otherwise defined, all technical and scientific terms used herein have the same meaning as is commonly understood by one of ordinary skill in the art to which this invention relates.

Although processes and materials similar or equivalent to those described herein can be used in the practice or testing of the present invention, the preferred processes and materials are described herein. In the case of inconsistencies, the present disclosure, including definitions, will control. In addition, the materials, processes, and examples are illustrative only and are not intended to be limiting.

The term "about" is used herein to mean approximately, in the region of, roughly, or around. When the term "about" is used in conjunction with a numerical range, it modifies that range by extending the boundaries above and below the numerical values set forth. The term "comprises" is used herein to mean "includes, but is not limited to."

The following abbreviations are used throughout the specification:

DHP: Dihydropyran Na$_2$SO$_4$: Sodium Sulphate
EtOAc: Ethyl Acetate Pd/C: Palladium on Carbon
HMPA: Hexamethylphosphoramide PPh$_3$: Triphenyl Phosphine
Im: Imidazole PTSA: p-toluenesolfonic acid
MeOH: Methanol THF: Tetrahydrofuran
n-BuLi: n-butyllithium THP: Tetrahydropyran
NaHCO$_3$: Sodium Carbonate In one non-limiting embodiment of the invention, an example of a 5 step synthetic process is provided for preparing $^{13}$C labeled iodotridecane of Formula A:

Formula A

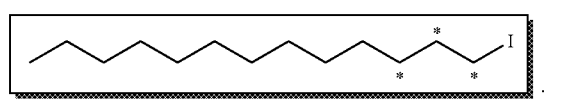

The synthetic process is depicted below in Scheme A.

Scheme A

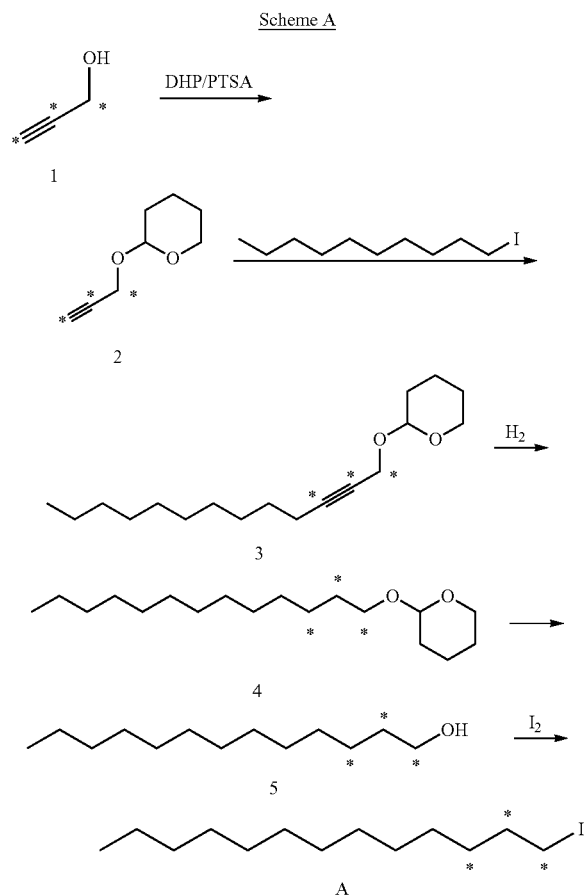

In this synthetic process, $^{13}$C labeled propargyl alcohol is used as a starting material. The alcohol group present in $^{13}$C labeled propargyl alcohol is protected as an ether group, and the resulting compound is alkylated with iododecane in the presence of n-BuLi/HMPA. The alkylated product is then hydrogenated, for instance using a catalyst such as Lindlar's catalyst, and deprotected to remove the tetrahydropyran (THP) in the presence of PTSA/MeOH. Finally, an iodination reaction is carried out, using I$_2$/PPh$_3$ and the product formed after deprotection, in order to produce $^{13}$C labeled iodotridecane.

EXAMPLES

The following provides examples of certain preferred embodiments of steps in the synthetic process described herein for producing the $^{13}$C iodotridecane of Formula A. The process is depicted below in Scheme B.

Scheme B

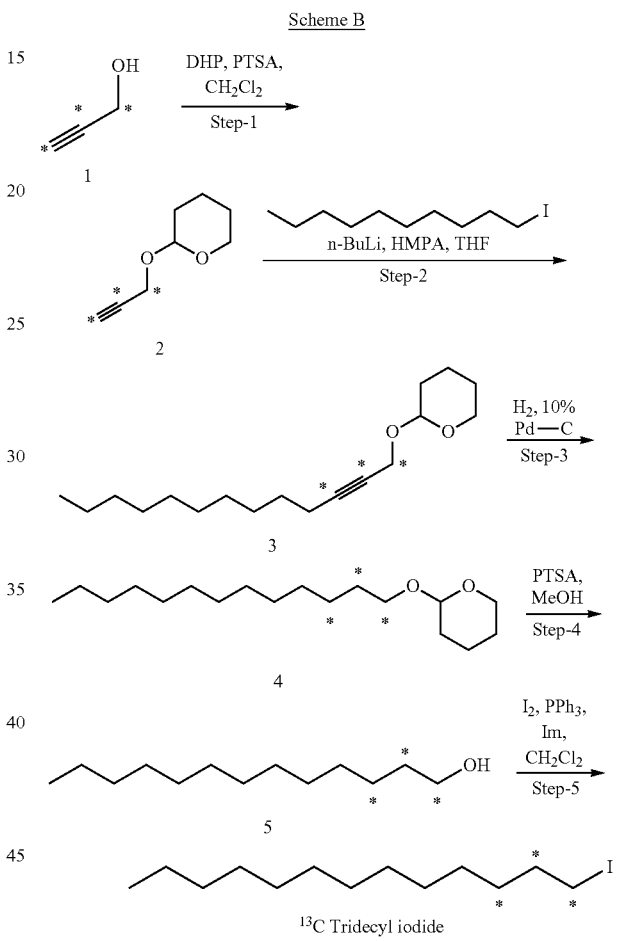

Preparation of a Compound Represented by Formula 2:

In the first step of the synthetic process, the primary alcohol present in $^{13}$C labeled propargyl alcohol was protected by ether bond formation, by reacting it with DHP/PTSA and resulting in a compound represented by Formula 2, the yield of the compound ranges from about 82-92%. The reaction scheme involved in this process is as follows:

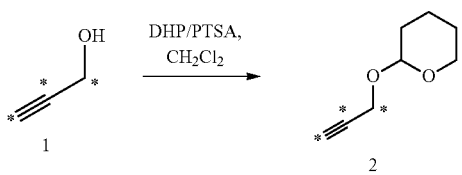

In an exemplary embodiment, the raw materials used for this process are illustrated in Table 1:

TABLE 1

| S. No. | Name of the Material | Qty. | M. Wt. | mmol | Mole Ratio |
|---|---|---|---|---|---|
| 1. | $^{13}$C labeled propargyl alcohol | 1 g | 56.06 | 16.93 | 1 |
| 2. | Dichloromethane | 15 mL | 84.93 | — | 15 vol. |
| 3. | PTSA | 3 mg | — | 0.16 | 0.009 |
| 4. | DHP | 3 mL | 84.12 | 33.86 | 2 |
| 5. | NaHCO$_3$ | — | 84.01 | — | — |
| 6. | Dichloromethane | 2 × 100 mL | 84.93 | — | 2 × 100 vol. |
| 7. | Water | 2 × 100 mL | 18 | — | 2 × 100 vol. |
| 8. | Brine | 1 × 100 mL | — | — | 100 vol. |

To a solution of $^{13}$C propargyl alcohol (1 g, 16.93 mmol) in dichloromethane (15 mL), PTSA (3 mg, 0.16 mmol) and DHP (3 mL, 33.86 mmol) were added and the reaction mixture was stirred at room temperature for 2 h. After completion of starting materials, the reaction mixture was quenched with NaHCO$_3$ and extracted with dichloromethane (100 mL×2), washed with water (100 mL×2), and brine (100 mL×1). The combined organic extracts were evaporated under reduced pressure to obtain the crude product which was purified by column chromatography (100-200 mesh silica gel, eluent 10% EtOAc in hexane) to furnish compound 2 (2.078 g, 87%) as a light brown liquid.

Preparation of a Compound Represented by Formula 3:

The compound represented by Formula 2 was alkylated with iododecane to obtain a compound to represented by Formula 3. In examples of this step, the yield of the compound ranges from 42-52%. The reaction scheme involved in this process is as follows:

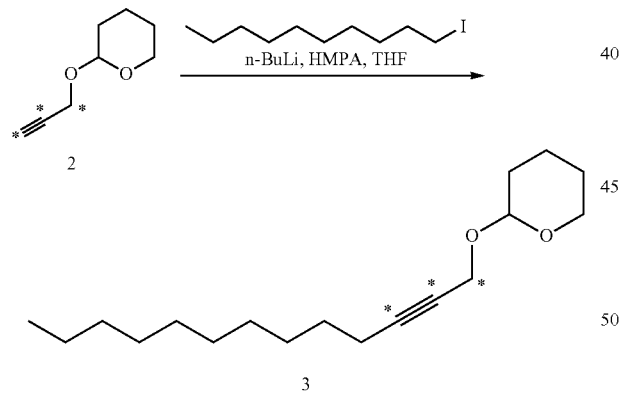

In an exemplary embodiment, the raw materials used for this process are illustrated in Table 2:

TABLE 2

| S. No. | Name of the Material | Qty. | M. Wt. | mmol | Mole Ratio |
|---|---|---|---|---|---|
| 1. | Compound of Formula 2 | 2.07 g | 142.76 | 14.5 | 1 |
|  | Iododecane | 3.8 mL | 268.18 | 17.4 | 1.2 |
| 2. | THF | 40 mL | 72.11 | — | 19.32 vol. |
| 3. | HMPA | 3.78 mL | 179.2 | 21.7 | 1.49 |
| 4. | n-BuLi | 7.54 mL | 64.06 | 18.86 | 1.3 |

TABLE 2-continued

| S. No. | Name of the Material | Qty. | M. Wt. | mmol | Mole Ratio |
|---|---|---|---|---|---|
| 5. | Ethyl acetate | 3 × 30 mL | 88.11 | — | 3 × 14.49 vol. |
| 7. | Water | 25 mL | 18 | — | 12.08 vol. |
| 8. | Brine | 25 mL | — | — | 12.08 vol. |
| 9. | Na$_2$SO$_4$, anhydrous | As needed | 142.04 | — | — |

To a solution of the compound represented by Formula 2 (2.07 g, 14.5 mmol) in THF (40 mL), HMPA (3.78 mL, 21.7 mmol) and n-BuLi (2.5 M, 7.54 mL, 18.86 mmol) were added drop wise at −78° C. After 1 hour, iododecane (3.8 mL, 17.4 mmol) in THF was added drop wise at −78° C. and stirred at room temperature for 16 h. After completion of starting materials, the reaction mixture was quenched with ice and extracted with ethyl acetate (30 mL×3), washed with water (25 mL×1), brine (25 mL×1) and dried over anhydrous Na$_2$SO$_4$. The combined organic extracts were evaporated under reduced pressure to obtain the crude product which was purified by column chromatography (100-200 mesh silica gel, eluent 10% Dichloromethane in hexane) to furnish the compound represented by Formula 3 (1.94 g, 47%) as a light yellow liquid.

Preparation of a Compound Represented by Formula 4:

Hydrogenation of the compound represented by Formula 3 resulted in a compound as represented by Formula 4. In examples of this step, the yield of the compound ranges from about 85-95%. The reaction scheme involved in this process is as follows:

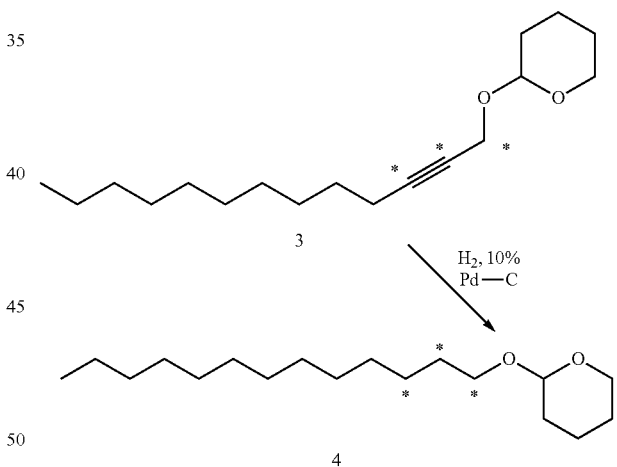

In an exemplary embodiment, the raw materials used for this process are illustrated in Table 3:

TABLE 3

| S. No. | Name of the Material | Qty. | M. Wt. | mmol | Mole Ratio |
|---|---|---|---|---|---|
| 1. | Compound of Formula 3 | 870 mg | 284.31 | 3.06 | 1 |
| 2. | Pd/C (10%) | 100 mg | — | — | — |
| 3. | Ethyl acetate | 2 × 30 mL | 88.11 | — | 2 × 9.8 vol. |

To a solution of the compound represented by Formula 3 (870 mg, 3.06 mmol) in ethyl acetate (10 mL), 10% Pd/C (100 mg) was added and the reaction was stirred under hydrogen atmosphere for 12 h. After completion of starting material, the reaction mass was filtered through a CeliteM pad and washed with ethyl acetate (30 mL×2) twice. The combined organic extracts were evaporated under reduced pressure to obtain the crude product which was purified by column chromatography (100-200 mesh silica gel, 5% ethyl acetate in hexane) to furnish the compound represented by Formula 4 (800 mg, 90%) as a colorless liquid.

Preparation of a Compound Represented by Formula 5:

THP present in the compound of Formula 4 was deprotected to produce the compound represented by Formula 5. In examples of this step, the yield of the compound ranges from about 85-95%. The reaction scheme involved in this process is as follows:

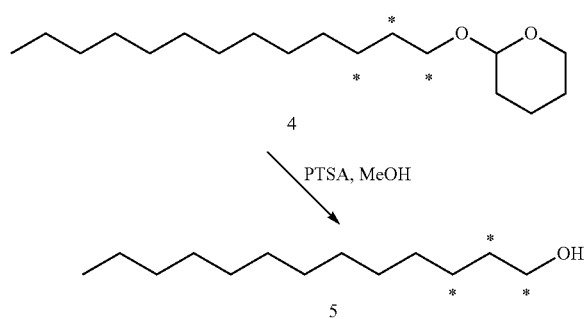

In an exemplary embodiment, the raw materials used for this process are illustrated in Table 4:

TABLE 4

| S. No. | Name of the Material | Qty. | M. Wt. | mmol | Mole Ratio |
|---|---|---|---|---|---|
| 1. | Compound of Formula 4 | 1.1 g | 287.96 | 3.82 | 1 |
| 2. | Methanol | 10 mL | 32 | — | 9.09 vol. |
| 3. | PTSA | 65 mg | — | 0.37 | 0.097 |
| 4. | NaHCO₃ | — | 84.01 | — | — |
| 5. | Ethyl acetate | 2 × 50 mL | 88.11 | — | 2 × 45.45 vol. |
| 6. | Water | 100 mL | — | — | 90.90 vol. |
| 7. | Brine | 50 mL | — | — | 45.45 vol. |
| 8. | Na₂SO₄ | As needed | 142.04 | — | — |

To a solution of compound represented by Formula 4 (1.1 g, 3.82 mmol) in methanol (10 mL), PTSA (65 mg, 0.37 mmol) was added and the reaction was stirred at room temperature for 2 h. After completion of starting material, the reaction mixture was quenched with NaHCO₃ and concentrated, extracted with ethyl acetate (50 mL×2) washed with water (100 mL×1), brine (50 mL×1) and dried over Na₂SO₄. The combined organic extracts were evaporated under reduced pressure to obtain the crude product which was purified by column chromatography (100-200 mesh silica gel, 30% dichloromethane in hexane) to furnish the compound represented by Formula 5 (700 mg, 90%) as a colorless liquid.

Preparation of a Compound Represented by Formula a:

The compound of Formula 5 was converted to the compound represented by Formula A by iodination of the primary alcohol present in the compound of Formula 5. In examples of this step, the yield of the compound ranges from about 80-88%. The reaction scheme involved in this process is as follows:

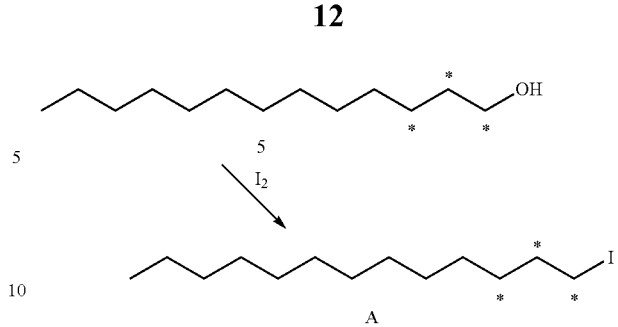

In an exemplary embodiment, the raw materials used for this process are illustrated in Table 5:

TABLE 5

| S. No. | Name of the Material | Qty. | M. Wt. | mmol | Mole Ratio |
|---|---|---|---|---|---|
| 1. | Compound of Formula 5 | 1.08 g | 203.39 | 5.31 | 1 |
| 2. | I₂ | 1.48 g | 253 | 5.84 | 1.1 |
| 3. | Dichloromethane | 20 mL | 84.93 | — | 18.52 vol. |
| 4. | Triphenyl phosphine | 1.53 g | 262.29 | 5.84 | 1.1 |
| 5. | Imidazole | 0.39 g | 68.07 | 5.84 | 1.1 |

To a solution of tridecanol (1.08 g, 5.31 mmol) in dichloromethane (20 mL), triphenyl phosphine (1.53 g, 5.84 mmol) and imidazole (0.39 g, 5.84 mmol) were added and cooled to 0° C. I₂ (1.48 g, 5.84 mmol) was added and the reaction mixture was stirred at room temperature for 3 h. After completion of starting materials, the reaction mixture was evaporated and diluted with hexane and passed through a Celite™ pad. The combined organic extracts were evaporated under reduced pressure to obtain the crude product which was purified by column chromatography (100-200 mesh silica gel, eluent hexane) to furnish compound A (1.43 g, 84%) as a low melting solid.

The preferred embodiments of the invention described above are merely exemplary of the invention, which can be embodied in various forms. Therefore, specific details relating to the reagents and reaction conditions disclosed herein are not to be interpreted as limiting, but merely as an example. It will also be apparent to a person skilled in the art that a number of variations and modifications can be made without departing from the scope of the invention as defined in the claims.

What is claimed is:

1. A process for preparing a ¹³C labeled haloalkane as represented by Formula (i):

Formula (i)

wherein R is a $C_1$-$C_{28}$ carbon chain, X is a halogen, and the compound of Formula (i) is ¹³C labeled at one or more of the carbon atoms labeled with an asterisk, the process comprising:
(a) protecting the primary alcohol present in ¹³C labeled propargyl alcohol by ether bond formation to obtain a compound of Formula (ii):

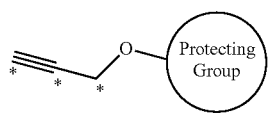
Formula (ii)

wherein the $^{13}C$ labeled propargyl alcohol is labeled at $C_1$, $C_2$ or $C_3$ thereof, or a combination thereof, and the compound of Formula (ii) is $^{13}C$ labeled at one or more of the carbon atoms labeled with an asterisk;

(b) alkylating the compound of Formula (ii) with X—R, wherein R is as defined above, and X is a halogen, to obtain a compound as represented by Formula (iii):

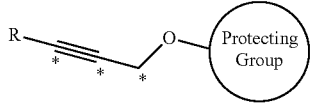
Formula (iii)

wherein the compound of Formula (iii) is $^{13}C$ labeled at one or more of the carbon atoms labeled with an asterisk;

(c) hydrogenating the compound of Formula (iii) to obtain a compound as represented by Formula (iv):

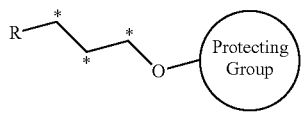
Formula (iv)

wherein the compound of Formula (iv) is $^{13}C$ labeled at one or more of the carbon atoms labeled with an asterisk;

(d) removing the protecting group in the compound of Formula (iv) to obtain the compound of Formula (v):

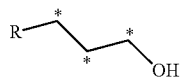
Formula (v)

wherein the compound of Formula (v) is $^{13}C$ labeled at one or more of the carbon atoms labeled with an asterisk; and (e) halogenating the primary alcohol present in the compound represented by Formula (v) to obtain the compound of Formula (i).

2. The process of claim 1, wherein R is a $C_5$-$C_{20}$ carbon chain.

3. The process of claim 1, wherein R is a $C_{10}$ alkyl chain.

4. The process of claim 1, wherein X is F, Cl, Br or I.

5. The process of claim 1, wherein X is I.

6. The process of claim 1, wherein the protecting group is a tetrahydropyran (THP) group.

7. The process of claim 1, wherein the compound of Formula (ii) is alkylated with a halodecane to obtain a compound as represented by Formula 3:

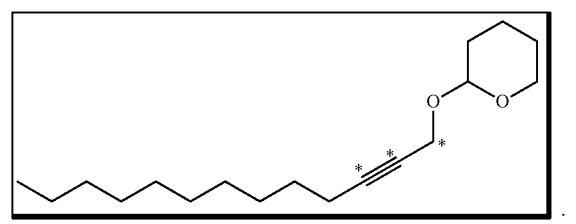
Formula 3

8. The process of claim 1, wherein two or three of the carbon atoms labeled with an asterisk are $^{13}C$ labeled.

9. The process of claim 6, wherein the $^{13}C$ labeled propargyl alcohol is reacted in step (a) with dihydropyran (DHP) and p-toluenesulfonic acid (PTSA) to produce a compound represented by Formula 2:

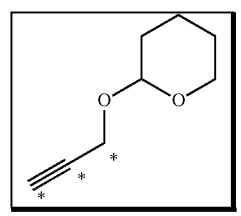
Formula 2

10. The process of claim 1, wherein the primary alcohol present in the compound represented by Formula (v) is halogenated by iodination.

11. A process for preparing a compound represented by Formula A:

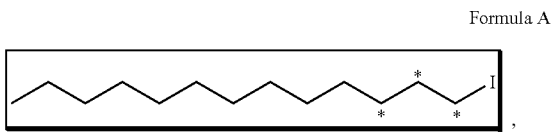
Formula A the process comprising the steps of:

(a) protecting the primary alcohol of a $^{13}C$ labeled propargyl alcohol of Formula 1:

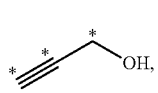
Formula 1 wherein the $^{13}C$ labeled propargyl alcohol of Formula 1 is labeled at one or more carbon atoms marked with an asterisk, using a protecting agent to obtain a compound represented by Formula 2:

Formula 2

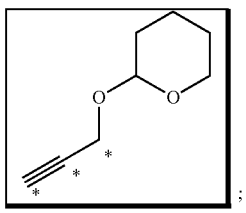

;

(b) alkylating the compound represented by Formula 2 with iododecane to yield a compound represented by Formula 3:

Formula 3

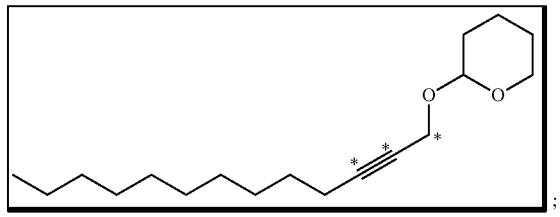

;

(c) hydrogenating the alkyne present in the compound represented by Formula 3 to yield a compound represented by Formula 4:

Formula 4

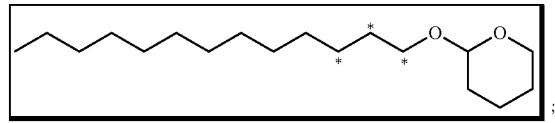

;

(d) removing the tetrahydropyran (THP) present in the compound represented by Formula 4 to yield a compound represented by Formula 5

Formula 5

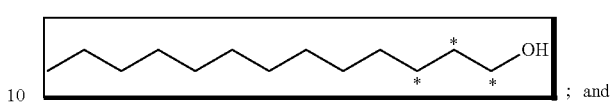

; and (e) iodinizing the primary alcohol present in the compound represented by Formula 5 to yield the compound represented by Formula A.

12. The process as claimed in claim 11, wherein step (a) is carried out in the presence of dichloromethane, dihydropyran (DHP) and p-toluenesulfonic acid (PTSA).

13. The process as claimed in claim 12, wherein the step (a) is carried out at about room temperature.

14. The process as claimed in claim 11, wherein the alkylation reaction of step (b) is carried out in the presence of tetrahydrofuran (THF), hexamethylphosphoramide (HPMA) and n-BuLi.

15. The process as claimed in claim 14, wherein the step (b) is carried out at a temperature of between about −78° C. to about room temperature.

16. The process as claimed in claim 11, wherein the hydrogenation reaction of step (c) is carried out in a hydrogen atmosphere in the presence of ethyl acetate and palladium on carbon (Pd/C).

17. The process as clamed in claim 11, wherein the reaction of step (d) is carried out in the presence of methanol and p-toluenesulfonic acid (PTSA).

18. The process as claimed in claim 17, wherein the reaction of step (d) is carried out at about room temperature.

19. The process as claimed in claim 11, wherein the iodinization reaction of step (e) is carried out in presence of dichloromethane, triphenyl phosphine and imidazole.

20. The process as claimed in claim 19, wherein the iodonization reaction of step (d) is carried out at a temperature of between about 0° C. to about room temperature.

* * * * *